(12) United States Patent
Guanche

(10) Patent No.: US 7,125,411 B2
(45) Date of Patent: Oct. 24, 2006

(54) CANNULA DELIVERY AND SUPPORT SYSTEM

(76) Inventor: Carlos A. Guanche, 19540 NW. 88 Ave., Miami, FL (US) 33018

( * ) Notice: Subject to any disclaimer, the term of this patent is extended or adjusted under 35 U.S.C. 154(b) by 245 days.

(21) Appl. No.: 10/714,168

(22) Filed: Nov. 14, 2003

(65) Prior Publication Data

US 2005/0107803 A1    May 19, 2005

(51) Int. Cl.
*A61B 17/34* (2006.01)
(52) U.S. Cl. ................ 606/108; 604/264; 128/DIG. 26
(58) Field of Classification Search ......... 128/DIG. 26
See application file for complete search history.

(56) References Cited

U.S. PATENT DOCUMENTS

| | | | |
|---|---|---|---|
| 1,419,268 A * | 6/1922 | Keeler, Sr. ................... 267/26 |
| 2,621,917 A * | 12/1952 | Landers ...................... 267/155 |
| 2,973,805 A * | 3/1961 | Rowan ....................... 267/142 |
| 3,338,538 A * | 8/1967 | Roche .......................... 248/75 |
| 4,461,102 A * | 7/1984 | DeVincentis ................. 36/101 |
| 4,593,681 A | 6/1986 | Soni |
| 4,624,672 A * | 11/1986 | Lenkauskas ................. 623/10 |
| 4,668,144 A * | 5/1987 | Giannuzzi .................... 411/342 |
| 5,197,971 A | 3/1993 | Bonutti |
| 5,207,683 A * | 5/1993 | Goode et al. ............... 606/108 |
| 5,234,455 A | 8/1993 | Mulhollan |
| 5,279,564 A * | 1/1994 | Taylor ......................... 604/104 |
| 5,637,097 A | 6/1997 | Yoon |
| 5,656,013 A | 8/1997 | Yoon |
| 5,697,946 A | 12/1997 | Hopper |
| 5,713,870 A | 2/1998 | Yoon |
| 5,735,867 A | 4/1998 | Golser |
| 5,810,836 A * | 9/1998 | Hussein et al. ............ 623/1.15 |
| 5,820,631 A * | 10/1998 | Nobles ........................ 606/213 |
| 5,882,340 A | 3/1999 | Yoon |
| 5,921,918 A | 7/1999 | Riza |
| 5,971,960 A | 10/1999 | Flom |
| 6,270,484 B1 | 8/2001 | Yoon |
| 6,443,957 B1 | 9/2002 | Addis |
| 6,524,283 B1 | 2/2003 | Hopper |

FOREIGN PATENT DOCUMENTS

SU    4422054    *    9/1992    ................... 36/101

* cited by examiner

*Primary Examiner*—Glenn K. Dawson
(74) *Attorney, Agent, or Firm*—Lawrence N. Ginsberg

(57) ABSTRACT

A cannula supporting coil that comprises a thin resilient elongated member having a proximal portion; an intermediate portion; and, a distal portion. The proximal portion of the thin resilient elongated member comprises a clip portion for capturing a side port of an endoscopic or arthroscopic cannula. The distal portion has a plurality of revolutions to accommodate the main body of the cannula. A terminal portion of a final revolution of the distal portion has less curvature than previous portions of the distal portion for anchoring to an anatomical cavity lining of an anatomical cavity. The cannula supporting coil is used as a component of a cannula delivery and support system that also includes an elongated sheath for containing the cannula supporting coil during delivery of the cannula supporting coil to the anatomical cavity; and, an elongated trocar contained within the sheath. Once the cannula delivery and support system is in the cavity the trocar is reinserted in an inverted position and utilized as a plunger for the cannula supporting coil.

29 Claims, 5 Drawing Sheets

CANNULA DELIVERY AND SUPPORT SYSTEM

BACKGROUND OF THE INVENTION

1. Field of the Invention

The present invention relates to anchor and anchoring systems for securing arthroscopic or laparoscopic cannulas within puncture openings in the skin and more particularly to a flexible coil to be secured to the cannula device after being inserted through the puncture opening.

2. Description of the Related Art

Arthroscopic or endoscopic surgery is that surgery performed through minimally-invasive means, through limited incisions. The areas that are approachable by these techniques include any synovial joint; the abdominal and thoracic cavities; the mediastinum, epidural, pleural and subarachnoid spaces; heart ventricles and spinal cavities.

These endoscopic procedures provide a minimally invasive approach to many surgical procedures previously performed through traditional means. In the traditional approaches, surgery was performed by making a large incision over the area, followed by an exposure of the area in question by retracting or incising the soft tissues between the skin and the necessary area. In endoscopic surgery, a small puncture is made in the skin and a series of instruments are inserted by way of cannulas directly into the area. The cannula devices that are employed are usually tubular in shape and are of various sizes. Many have serrations, protruberances or threads at their tips (U.S. Pat. No. 5,217,441), in order to stabilize them in the soft tissues. None of the available designs, however, are effective in maintaining the cannula in proper position.

The reason for the lack of stability is that most commonly there is a medium that is used to distend the space. In the abdominal and thoracic cavities, it is $CO_2$ gas; while in joints, it is saline solution. These materials cause the tissues to deform, subsequently allowing the cannula devices to move out of their original positions. The most common problem is that of having to re-insert the device back through the previously made tract. This becomes increasingly difficult with the use of more gas or fluid for distention.

There are several devices available that attempt to improve the stability of the cannula devices. One such example is U.S. Pat. No. 6,542,283 (Hopper), in which a universal balloon anchor is employed for stabilization of the cannula device. The complexity of the device, however, precludes its common employment as a result of its prohibitive price.

Many other devices are available that attempt to improve stability of the cannula by incorporating the stabilizing elements into the cannula. Some examples are U.S. Pat. No. 5,637,097 (Yoon), U.S. Pat. No. 5,197,971 (Bonutti), U.S. Pat. No. 5,002,557 (Hasson) and U.S. Pat. No. 5,882,340 (Yoon). All of these, while perhaps stabilizing the devices nicely, are not commonly employed as a result of their prohibitive cost, compared to the standard cannula devices currently available.

SUMMARY OF THE INVENTION

In a broad aspect, the present invention is a cannula supporting coil that comprises a thin resilient elongated member having a proximal portion; an intermediate portion; and, a distal portion. The proximal portion of the thin resilient elongated member comprises a clip portion for capturing a side port of an endoscopic or arthroscopic cannula. The distal portion has a plurality of revolutions to accommodate the main body of the cannula. A terminal portion of a final revolution of the distal portion has less curvature than previous portions of the distal portion for anchoring to an anatomical cavity lining of an anatomical cavity.

In another broad aspect the present invention is a cannula delivery and support system that includes the cannula supporting coil discussed above, an elongated sheath for containing said cannula supporting coil during delivery of the cannula supporting coil to the anatomical cavity; and an elongated trocar. An upper portion of the trocar has a diameter slightly smaller than an inner surface of the elongated sheath. A lower portion has a diameter less than the revolutions of the distal portion of the cannula supporting coil so as to maintain the revolutions of the distal portion of the cannula supporting coil about the lower portion. The lower portion terminates in an atraumatic end.

The lower portion of the trocar, the sheath, and the cannula supporting coil are introduced into the anatomical cavity as a single unit, the trocar being removed and inverted so that the upper end thereof is utilized as a plunger to push the cannula supporting coil toward a lower end of the elongated sheath thus allowing removal of the sheath to allow placement of the cannula supporting coil and subsequent placement of the cannula.

The present invention is an improvement over the prior art in that it provides for a flexible device that is inserted prior to insertion of the cannula device, then locks onto the side portal of the cannula and stabilizes it. The device is universal in its ability to support many varieties of cannulas that are inserted into body spaces.

DETAILED DESCRIPTION OF THE INVENTION

Figure 1:
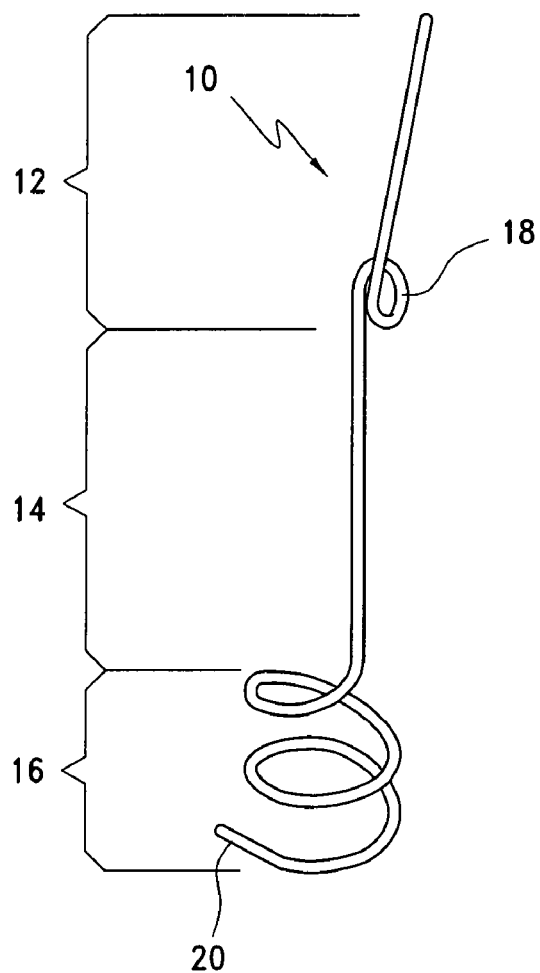
FIG. 1 is a perspective view of the cannula supporting coil of the present invention.

Referring now to the drawings and the characters of reference marked thereon, FIG. 1 illustrates a preferred embodiment of the cannula supporting coil the present invention, designated generally as 10. The cannula supporting coil 10 comprises a thin resilient elongated member including a proximal portion 12, an intermediate portion 14 and a distal portion 16. The proximal portion 12 includes a clip portion 18 for capturing a side port of an endoscopic or arthroscopic cannula. The clip portion 18 may comprise a loop of the elongated member. The loop may have, for example, a diameter of about 5mm. The distal portion 16 preferably has a plurality of revolutions to accommodate the main body of the cannula There are generally about 2–5 revolutions, preferably about three. A terminal portion 20 of a final revolution of the distal portion 16 has less curvature than previous portions of the distal portion 16 for anchoring to an anatomical cavity having an anatomical cavity lining. It is preferably straight to assure its purchase In tissues.

The cannula supporting coil 10 is preferably formed of a metal wire such as nitinol, a shape memory alloy. Nitinol exhibits a unique phase transformation in the crystal structure when transitioning between the austenite and martensite phases. The austenite phase is the high temperature, stronger state compared to the weaker, low temperature martensite phase. Nitinol is comprised mostly of nickel and titanium, and usually alloyed with various other metals. It is the most common shape memory alloy; however, numerous alloys behave in a similar fashion. Alternatively, other resilient materials may be used such as plastic that have the ability to maintain the desired configuration. The coil 10 preferably has a diameter in a range of 1–5 mm, most preferably about 2 mm. It may be, for example, about 90 mm long and have rounded (or smooth) tips. The length, L1, of the sum of the proximal and intermediate portions 12,14 may be, for example, about 70 mm. The length, L2, of the distal portion 16 may be about 25 mm.

Figure 2:
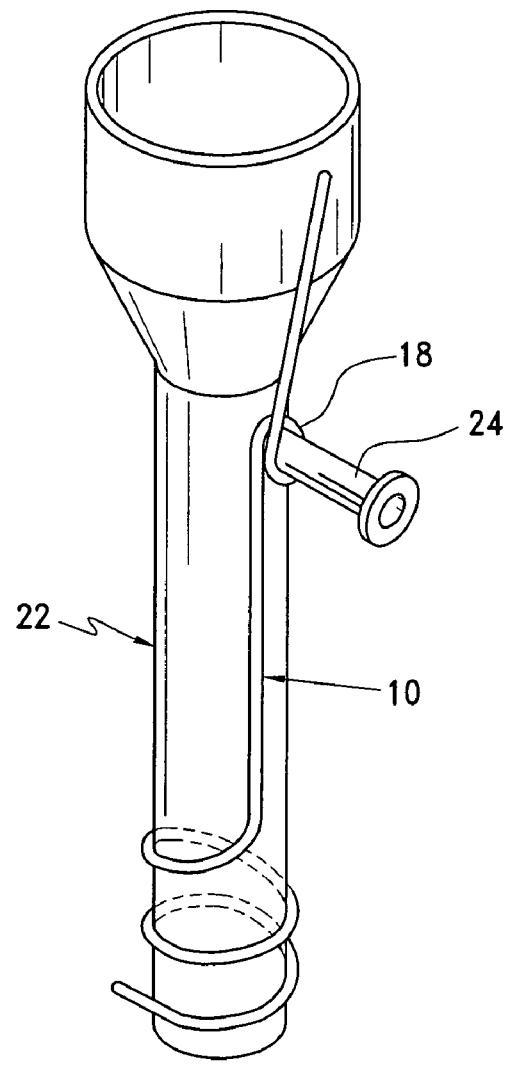
FIG. 2 is a perspective view of the cannula supporting coil in place around an arthroscopic cannula.

Referring now to FIG. 2, the cannula supporting coil 10 is shown in place about a cannula 22, as will be described in more detail below. The clip portion 18 of the cannula supporting coil 10 is wrapped around a side port 24 of the cannula 22. The distal portion 16 of the cannula supporting coil 10 anchors to an anatomical cavity lining.

Figure 3:
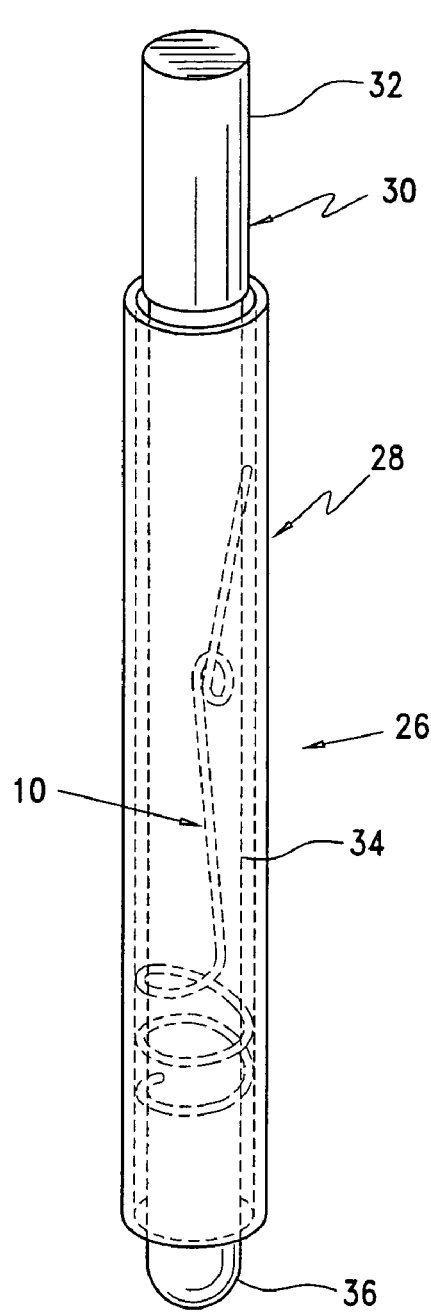
FIG. 3 is a perspective view, partially in phantom, of the cannula delivery and support system of the present invention.

Referring now to FIG. 3, the entire cannula delivery and support system, designated generally as 26, is illustrated. The cannula delivery and support system 26 includes the cannula supporting coil 10, an elongated sheath 28, and an elongated trocar 30. The elongated sheath 28 contains the cannula supporting coil 10 during delivery of the cannula supporting coil 10 to the anatomical cavity. The elongated trocar 30 has an upper portion 32 and a lower portion 34. The upper portion 32 has a diameter slightly smaller than an inner surface of the elongated sheath 28. The lower portion 34 has a diameter less than the revolutions of the distal portion of the cannula supporting coil 10 so as to maintain the revolutions of the distal portion 16 of the cannula supporting coil 10 about the lower portion 34. The lower portion 34 terminates in an atraumatic end 36. The elongated sheath 28 is preferably formed of metal or plastic.

Figure 4:
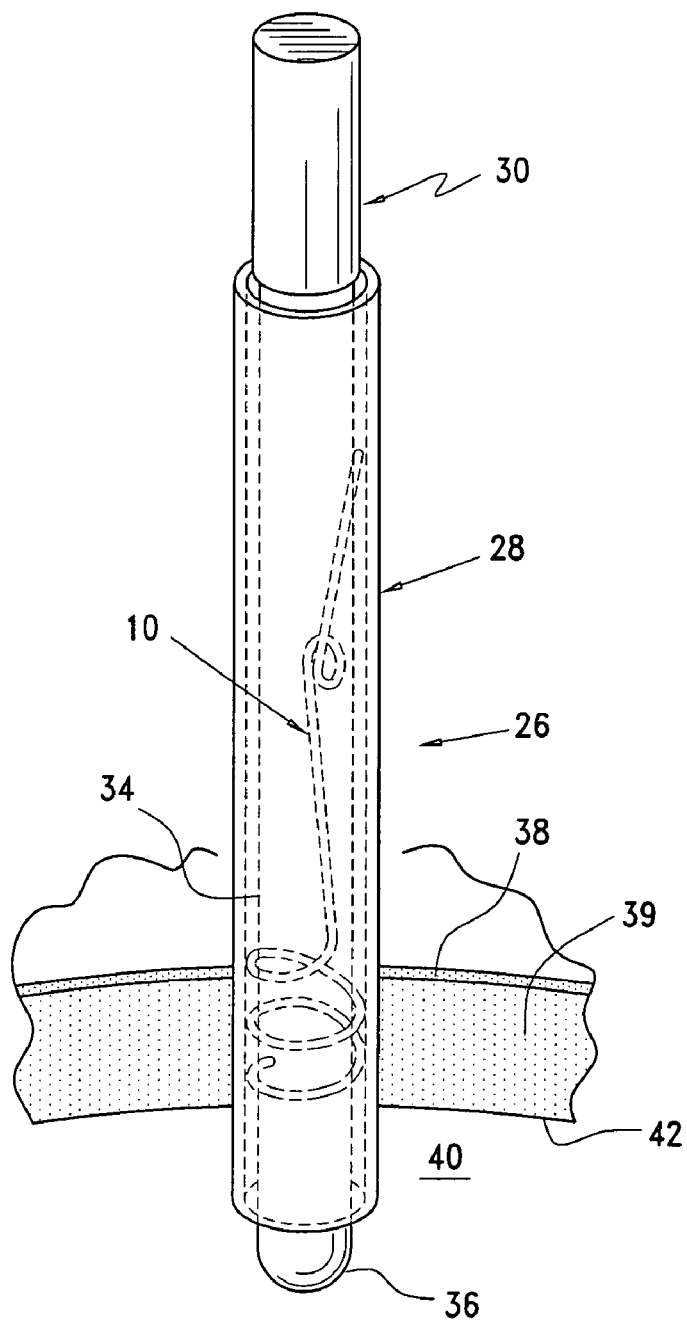
FIG. 4 is a perspective view, partially in cross-section and in phantom, of the cannula delivery and support system positioned in a joint space.

In operation, an incision is made in the skin of a patient. The incision is utilized for inserting the cannula delivery and support system 26 into an anatomical cavity. As can be seen in FIG. 4, the incision in the skin 38 is used to insert the cannula delivery and support system 26 into the soft tissue 39 between the skin 38 and the anatomical cavity 40 which is surrounded by the cavity lining 42. The system 26 includes the elongated sheath 28 that contains the cannula supporting coil 10. It also includes the elongated trocar 30. Elongated trocar 30 sits within the elongated sheath 28, so that, as noted above, the revolutions of the distal portion 16 of the cannula supporting coil 10 are maintained about the lower portion 34 of the trocar 30. The edges of the sheath 28 should preferably have slightly tapered edges to prevent catching through tissues.

Figures 5, 6:
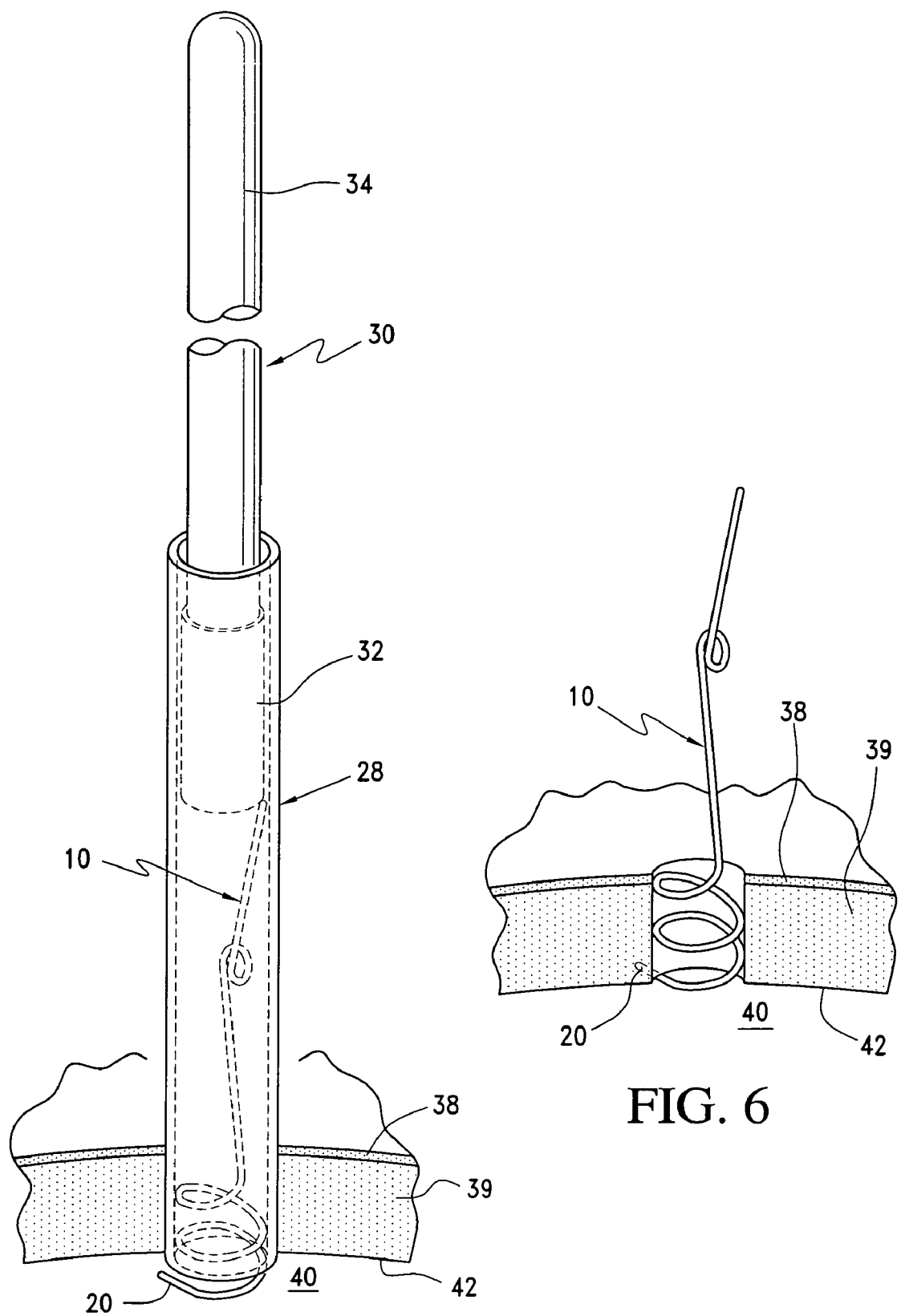
FIG. 5 is a partially cutaway side perspective view showing the advancement of a cannula supporting coil into the joint space by use of a plunger portion of the trocar.
FIG. 6 is a partially cutaway side perspective view of the cannula supporting coil in position within a joint.

Referring now to FIG. 5, once the cannula delivery and support system 26 is in the cavity 40 the trocar 30 is pulled out and inverted. The trocar 30 is then reinserted into the elongated sheath 28 in the inverted position so that the upper end 32 thereof is utilized as a plunger to push the cannula supporting coil 10 toward a lower end of the elongated sheath 28 so that the terminal portion 20 of the cannula supporting coil 10 is within the anatomical cavity 40.

As can be seen in FIG. 6, once the cannula supporting coil 10 is in place with the distal portion in the joint, the elongated sheath 28 is removed leaving the cannula supporting coil 10 within the anatomical cavity 40 to the cavity lining 42.

Figures 7, 8:
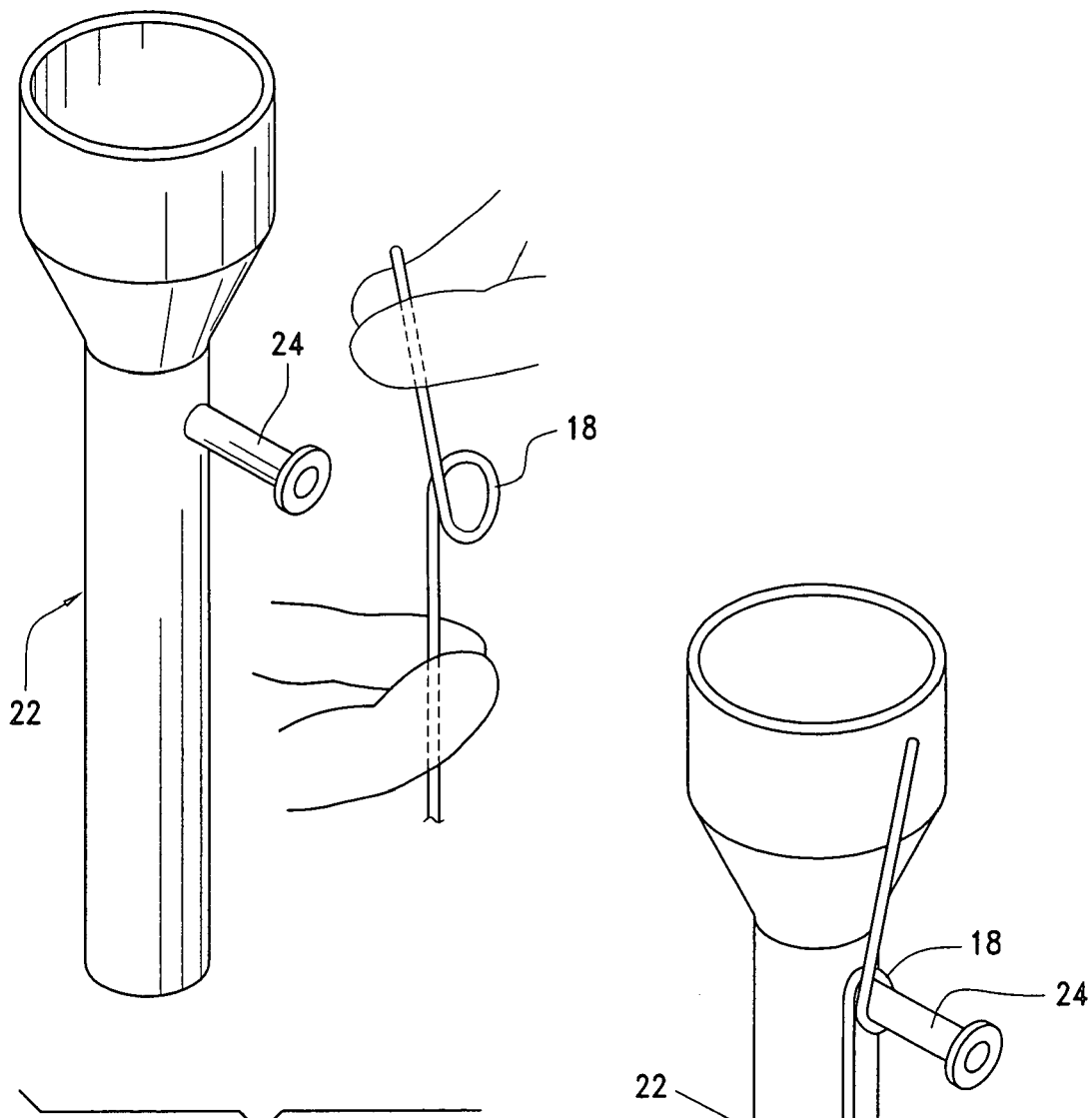
FIG. 7 is a schematic illustration of the clip portion of the cannula supporting coil being positioned over a side port of the cannula.
FIG. 8 is a schematic illustration of a cannula positioned within a cannula supporting coil, with the clip portion in place on a cannula side port.

Referring now to FIGS. 7 and 8, once the elongated sheath 28 is removed, the cannula 22 is inserted into the anatomical cavity 40 within the revolutions and the clip portion 18 of the cannula supporting coil 10 is inserted about the side port 24 of the cannula 22. The loop 18 is thus placed at about 90 degrees to the rest of the cannula. Alternatively, a locking sleeve can be applied circumferentially around the coil and cannula in order to stabilize the device (this can be as simple as steri-strips). This portion is variable as the design of many cannulas varies from one surgical discipline to another.

FIG. 8 shows the cannula 22 positioned within the cannula supporting coil 10, with the clip portion 18 in place on the side port 24.

The present device/method may be useful in arthroscopic surgery of any joint, endoscopic surgery of the abdomen, pelvis, chest and mediastinum. It may be used in a synovial joint, thoracic cavity, epidural space, pleural space, subarachnoid space, heart ventricle, spinal cavity.

Other embodiments and configurations may be devised without departing from the spirit of the invention and the scope of the appended claims. For example, referring now to FIGS. 9A and 9B, another embodiment of the trocar is illustrated, designated generally as 42. The trocar 42 has an upper portion 44 with a truncated circular cross-section. This is preferably about ¾ of a circle.

Figures 9A, 9B, 10:
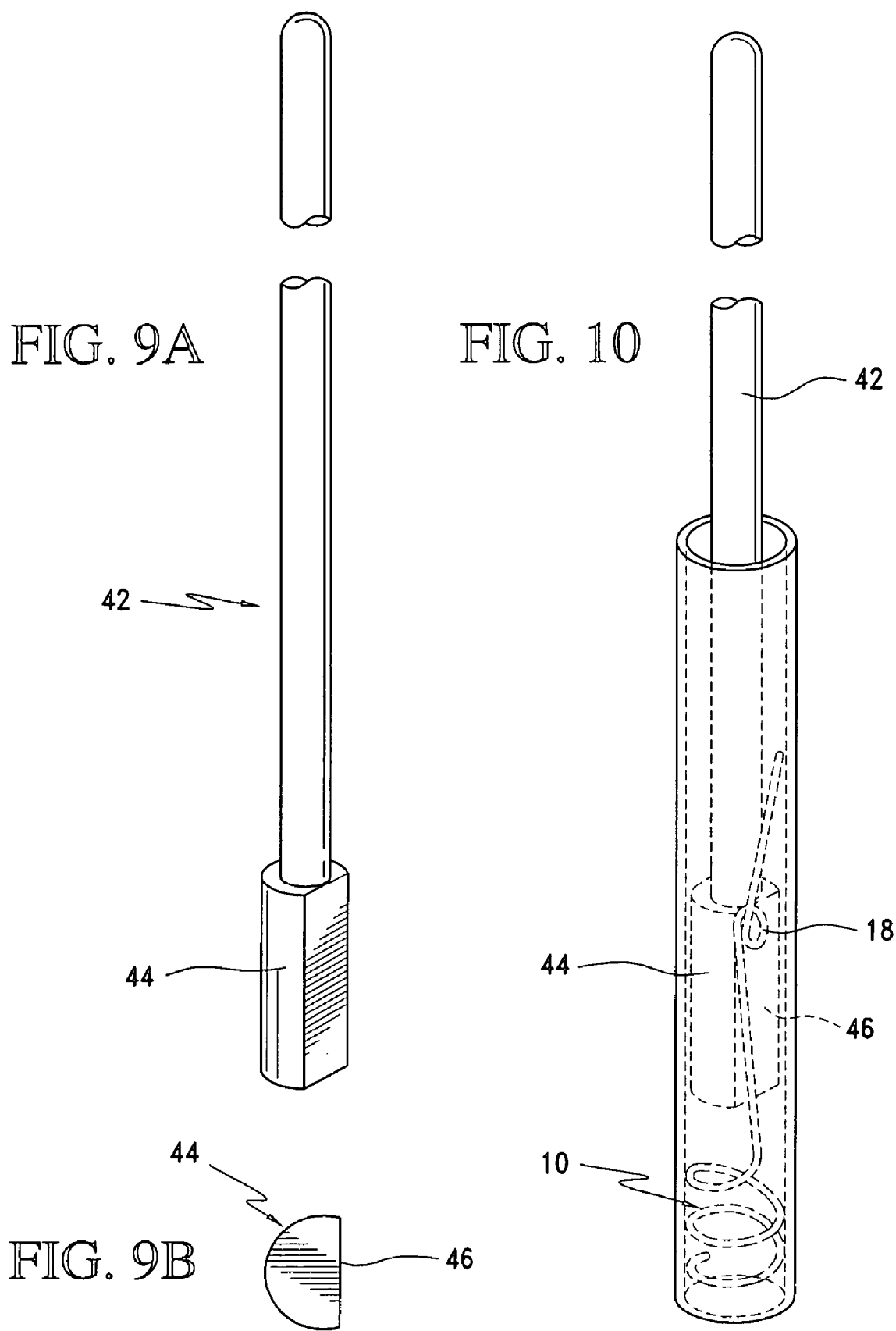
FIG. 9A is a perspective view of an alternate trocar.
FIG. 9B is an end view of the trocar of FIG. 9A.
FIG. 10 is a side perspective view showing the advancement of a cannula supporting coil within the cannula by use of the trocar of FIGS. 9A and 9B.

Thus, in use, as can be seen in FIG. 10, the trocar 42 is inverted. The space between the truncated portion 46 and the wall of the elongated sheath can accommodate the clip portion 18 of the cannula supporting coil 10. Therefore, the end of the trocar 42 engages only the distal portion of the cannula supporting coil 10. The coil 10 may be advanced without distorting the clip portion 18 of the coil 10.

The invention claimed is:

1. A cannula delivery and support system, comprising:
   a) a cannula supporting coil comprising:
      a thin resilient elongated member, comprising:
      i) a proximal portion comprising a clip portion for capturing a side port of an endoscopic or arthroscopic cannula;
      ii) an intermediate portion; and,
      iii) a distal portion having a plurality of revolutions to accommodate the main body of the cannula, a terminal portion of a final revolution of said distal portion
      having less curvature than previous portions of said distal portion for anchoring to
      an anatomical cavity lining of an anatomical cavity;
   b) an elongated sheath for containing said cannula supporting coil during delivery of said cannula supporting coil to the anatomical cavity; and, c) an elongated trocar having an upper portion and a lower portion, said upper portion having an outer surface slightly smaller tan an inner surface of said elongated sheath, said lower portion having a diameter less than said revolutions of said distal portion of said cannula supporting coil so as to maintain said revolutions of said distal portion of said cannula supporting coil about said lower portion, said lower portion terminating in an atraumatic end, wherein said lower portion of said trocar, said sheath, and said cannula supporting coil are introduced into the anatomical cavity as a single unit, said trocar being removed and inverted so that said upper end thereof is utilized as a plunger to push the cannula supporting coil toward a lower end of said elongated sheath thus allowing removal of said sheath to allow placement of said cannula supporting coil and subsequent placement of the cannula.

2. The cannula delivery and support system of claim 1 wherein said elongated sheath is formed of metal.

3. The cannula delivery and support system of claim 1 wherein said elongated sheath is formed of plastic.

4. The cannula delivery and support system of claim 1 wherein said elongated sheath has a blunt end.

5. The cannula delivery and support system of claim 1 wherein said elongated sheath has a diameter in a range of between about 8 and 25 mm.

6. The cannula delivery and support system of claim 1 wherein said upper portion of said trocar has a circular cross-section with a diameter in a range of between 8 and 25 mm.

7. The cannula delivery and support system of claim 1 wherein said lower portion of said trocar has a circular cross-section with a diameter in a range of between 5 and 15 mm.

8. The cannula delivery and support system of claim 1 wherein said upper portion of said trocar has a truncated circular cross-section.

9. The cannula delivery and support system of claim 1 wherein said upper portion of said trocar has a truncated circular cross-section of about ¾ of a circle.

10. The cannula supporting coil of claim 1 wherein said terminal portion of said final revolution is substantially straight.

11. The cannula supporting coil of claim 1 wherein said thin resilient elongated member comprises memory wire.

12. The cannula supporting coil of claim 1 wherein said thin resilient elongated member comprises Nitinol memory wire.

13. The cannula supporting coil of claim 1 wherein said thin resilient elongated member is formed of plastic.

14. The cannula supporting coil of claim 1 wherein said thin resilient elongated member comprises wire having a diameter in a range of 1–5 mm.

15. The cannula supporting coil of claim 1 wherein said thin resilient elongated member comprises wire having a diameter about 2 mm.

16. The cannula supporting coil of claim 1 wherein said plurality of revolutions is in a range of 2–5.

17. The cannula supporting coil of claim 1 wherein said plurality of revolutions comprises 3 revolutions.

18. The cannula supporting coil of claim 1 wherein said clip portion comprises a loop of said thin resilient elongated member for wrapping around the side port of the cannula.

19. The cannula supporting coil of claim 1 wherein said clip portion comprises a loop of said thin resilient elongated member for wrapping around the side port of the cannula, said loop having a diameter of about 5mm.

20. A method for delivering and supporting a cannula within an anatomical cavity, comprising the steps of:
  a) making an incision in the skin of a patient;
  b) utilizing said incision for inserting a cannula delivery and support system into an anatomical cavity, said cannula delivery and support system, comprising:
    i. a cannula supporting coil comprising:
      a thin resilient elongated member, comprising:
        a) a proximal portion comprising a clip portion for capturing a side port of an endoscopic or arthroscopic cannula;
        b) an intermediate portion; and,
        c) a distal portion having a plurality of revolutions to accommodate the main body of the cannula, a terminal portion of a final revolution of said distal portion having less curvature than previous portions of said distal portion for anchoring to an anatomical cavity lining of the anatomical cavity;
    ii. an elongated sheath for containing said cannula supporting coil during delivery of said cannula supporting coil to the anatomical cavity; and,
    iii. an elongated trocar having an upper portion and a lower portion, said upper portion having an outer surface slightly smaller than an inner surface of said elongated sheath, said lower portion having a diameter less than said revolutions of said distal portion of said cannula supporting coil so as to maintain said revolutions of said distal portion of said cannula supporting coil about said lower portion, said lower portion terminating in an atraumatic end;
  c) pulling said elongated trocar out of said elongated sheath;
  d) inverting said elongated trocar and reinserting it into said elongated sheath in said inverted position so that said upper end thereof is utilized as a plunger to push the cannula supporting coil toward a lower end of said elongated sheath so that said terminal portion of said cannula supporting coil anchors to said anatomical cavity lining;
  e) removing said sheath from said anatomical cavity lining leaving said cannula supporting coil within said anatomical cavity;
  f) inserting a cannula into said anatomical cavity within said revolutions; and,
  g) placing said clip portion of said cannula supporting coil about a side port of the cannula.

21. The method of claim 20 wherein said step of inserting a cannula delivery and support system into said anatomical cavity comprises inserting said cannula delivery and support system into a synovial joint.

22. The method of claim 20 wherein said step of inserting a cannula delivery and support system into said anatomical cavity comprises inserting said cannula delivery and support system into an abdominal cavity.

23. The method of claim 20 wherein said step of inserting a cannula delivery and support system into said anatomical cavity comprises inserting said cannula delivery and support system into a thoracic cavity.

24. The method of claim 20 wherein said step of inserting a cannula delivery and support system into said anatomical cavity comprises inserting said cannula delivery and support system into a mediastinal space.

25. The method of claim 20 wherein said step of inserting a cannula delivery and support system into said anatomical cavity comprises inserting said cannula delivery and support system into a epidural space.

26. The method of claim 20 wherein said step of inserting a cannula delivery and support system into said anatomical cavity comprises inserting said cannula delivery and support system into a pleural space.

27. The method of claim 20 wherein said step of inserting a cannula delivery and support system into said anatomical cavity comprises inserting said cannula delivery and support system into a subarachnoid space.

28. The method of claim 20 wherein said step of inserting a cannula delivery and support system into said anatomical cavity comprises Inserting said cannula delivery and support system into a heart ventricle.

29. The method of claim 20 wherein said step of inserting a cannula delivery and support system into said anatomical cavity comprises inserting said cannula delivery and support system into a spinal cavity.

* * * * *